(12) United States Patent
Beckett et al.

(10) Patent No.: US 6,310,084 B1
(45) Date of Patent: *Oct. 30, 2001

(54) METALLOPROTEINASE INHIBITORS

(75) Inventors: Raymond Paul Beckett; Fionna Mitchell Martin; Richard Simon Todd, all of Cowley (GB)

(73) Assignee: British Biotech Pharmaceuticals Limited, Oxford (GB)

(*) Notice: Subject to any disclaimer, the term of this patent is extended or adjusted under 35 U.S.C. 154(b) by 0 days.

This patent is subject to a terminal disclaimer.

(21) Appl. No.: 09/424,290

(22) PCT Filed: May 19, 1998

(86) PCT No.: PCT/GB98/01445

§ 371 Date: Feb. 11, 2000

§ 102(e) Date: Feb. 11, 2000

(87) PCT Pub. No.: WO98/52910

PCT Pub. Date: Nov. 26, 1998

(30) Foreign Application Priority Data

May 21, 1997 (GB) .................................... 9710490

(51) Int. Cl.⁷ ...................... C07C 229/04; C07C 229/38; C07C 62/38; A61K 31/195; A61K 31/415

(52) U.S. Cl. .......................... 514/396; 514/415; 514/561; 514/563; 514/567; 548/300.1; 549/469; 562/444; 562/504; 562/621; 562/622; 562/623

(58) Field of Search ..................................... 562/444, 504, 562/621, 622, 623; 514/561, 563, 567, 396, 415; 548/300.1; 549/469

(56) References Cited

U.S. PATENT DOCUMENTS

| | | | | |
|---|---|---|---|---|
| 5,665,753 | * | 9/1997 | Frazee et al. | 514/394 |
| 5,840,974 | * | 11/1998 | Whittaker et al. | 560/448 |
| 6,147,114 | * | 11/2000 | Fujisawa et al. | 514/575 |
| 6,172,064 | * | 1/2001 | Andrews et al. | 514/237.8 |

FOREIGN PATENT DOCUMENTS 96 16027 5/1996 (WO) .

* cited by examiner

Primary Examiner—Gary Geist
Assistant Examiner—Leigh C. Maier
(74) Attorney, Agent, or Firm—Banner & Witcoff, Ltd.

(57) ABSTRACT

The present invention relates to therapeutically active hydroxamic acid, N-formyl-N-hydroxyamino and carboxylic acid derivatives, their preparation, and pharmaceutical compositions containing them. These compounds are useful in the inhibition of metalloproteases, such as stromelysin, gelatinase, matrilysin, and collagenase. These compounds are useful in the treatment of mammals having disease-states alleviated by the inhibition of such matrix metalloproteases.

19 Claims, No Drawings

METALLOPROTEINASE INHIBITORS

The present invention relates to therapeutically active hydroxamic acid and carboxylic acid derivatives, to processes for their preparation, to pharmaceutical compositions containing them, and to the use of such compounds in medicine. In particular, the compounds are inhibitors of metalloproteases involved in tissue degradation.

BACKGROUND TO THE INVENTION

The matrix metalloproteinases (MMPS) are a family of enzymes including interstitial collagenase, neutrophil collagenase, collagenase-3, 72 kDa gelatinase, 92 kDa gelatinase, stromelysin-1, stromelysin-2, stromelysin-3, matrilysin, macrophage metalloelastase, membrane-type metalloproteinase-1 and membrane-type metalloproteinase-2. These enzymes share a common zinc-containing catalytic domain and a pro-sequence which maintains latency. A wide range of cells and tissues can express MMPs in response to activation by inflammatory stimuli such as interleukin-1 or tumour necrosis factor-α (TNF-α). Different stimuli can induce overlapping yet distinct repertoires of MMPs and different cell types can respond to the same stimuli by expression of distinct combinations of MMPs. MMPs can attack the protein components of extracellular matrix such as collagens, vitronectin and elastin, and have recently been shown to process membrane proteins such as pro-TNF-α to release soluble TNF-α. MMPs are thought to play a central role in the pathology of inflammatory diseases such as rheumatoid arthritis as well as in the growth and metastasis of tumours.

Compounds which have the property of inhibiting the action of MMPs are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas.

Two known classes of pseudopeptide or peptide mimetic MMP inhibitors have a hydroxamic acid group or a carboxylic group respectively as their zinc binding groups. Many such known MMPs may be represented by the structural formula (IA)

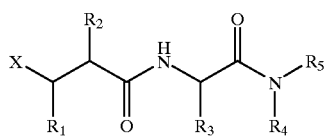

(IA)

in which X is the zinc binding hydroxamic acid (—CONHOH) or carboxylic acid (—COOH) group and the groups $R_1$ to $R_5$ are variable in accordance with the specific prior art disclosures of such compounds.

WO 96/16027 (Syntex/Agouron) discloses a class of MMP inhibitor compounds which can be represented by formula (IA) above. The principal structural characterising feature of the compounds disclosed in WO 96/16027 is the group $R_2$ which is defined in the publication as being a group $R^2$—X— wherein X is —$(CH_2)_m$—Y—$(CH_2)_n$, Y being O, S or a single bond, m and n being 0, 1, 2, 3 or 4 and m+n being 0, 1, 2, 3, or 4, and $R^2$ being (inter alia) aryl or heteroaryl, the latter terms including biaryl such as biphenyl and heteroaryl-aryl such as 4-pyridylphenyl.

Another known class of collagenase inhibitors is represented by those disclosed in EP-A-0574758 (Roche), EP-A-0684240 (Roche), and WO 95/33731 (Roche). In general, the compounds disclosed in those publications may be represented by the structural formula (IB):

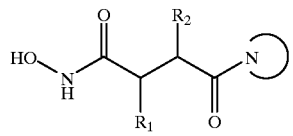

(IB)

in which $R_1$, $R_2$ and the N-containing ring are variable in accordance with the specific disclosures of the publications.

M. A. Abreo et al. presented a poster entitled "Truncated Succinamide Hydroxamates With Nanomolar Potency against various MMPs" at the 213th ACS Meeting in San Francisco, Apr. 13th–17th 1997. In that poster compounds of formula (IC) were disclosed:

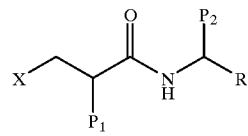

(IC)

wherein X is —COOH or —CONHOH, $P_1$ is biphenylpropyl, R is hydroxymethyl and $P_2$ is the side chain found in one of the following amino acids, namely serine, tert-butylglycine, histidine, O-benzylthreonine, phenylalanine, tyrosine, methionine, threonine, and 3-(3-pyridyl)alanine. Also disclosed were compounds of formula (IC) wherein X and $P_1$ are as just defined, and $P_2$ and R together with the carbon atom to which they are attached form a trans-cyclohexane-2-ol or glucosyl ring. The authors stated that the compound (IC), $P_2$=the histidine side chain and R=hydroxymethyl, showed good plasma levels after iv and oral dosing to mice. They also stated that the X-ray crystal structure of compound (IC), $P_2$=tert-butyl and R=hydroxymethyl, was obtained with stromelysin-1, and that the hydroxyl moiety in R makes an H-bond in the $P_3$ area of the enzyme, while the tert-butyl group makes good hydrophobic contact in the $P_2$ area.

BRIEF DESCRIPTION OF THE INVENTION

The present invention makes available a novel class of MMP inhibitors with a hydroxamic acid or carboxylic acid zinc binding group X, differing in structure from compounds (IC) above principally by the presence of a cycloalkyl, cycloalkenyl or non-aromatic heterocyclic substituent on the carbon atom carrying the group X. Compounds (IA) and (IB) known in the art do not include those with $R_1$=cycloalkyl, cycloalkenyl or non-aromatic heterocyclic. Compounds of the new class have good inhibitory potencies against various MMP enzymes. The class includes compounds with appropriate aqueous solubility, pKa, log P and molecular weight for good oral absorption.

DETAILED DESCRIPTION OF THE INVENTION

The present invention provides compounds of general formula (I)

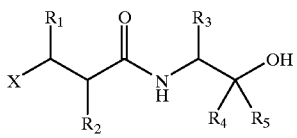

(I)

wherein:

X is a —CO₂H or —CONHOH group;

R₁ is a cycloalkyl, cycloalkenyl or non-aromatic heterocyclic ring containing up to 3 heteroatoms, any of which may be (i) substituted by one or more substituents selected from $C_1$–$C_6$ alkyl, $C_2$–$C_6$ alkenyl, halo, cyano (—CN), —CO₂H, —CO₂R, —CONH₂, —CONHR, —CON(R)₂, —OH, —OR, oxo-, —SH, —SR, —NHCOR and —NHCO₂R wherein R is $C_1$–$C_6$ alkyl or benzyl and/or (ii) fused to a cycloalkyl or heterocyclic ring;

R₂ is a $C_1$–$C_{12}$ alkyl, $C_2$–$C_{12}$ alkenyl, $C_2$–$C_{12}$ alkynyl, phenyl($C_1$–$C_6$ alkyl)-, heteroaryl($C_1$–$C_6$ alkyl)-, cycloalkyl($C_1$–$C_6$ alkyl)-, cycloalkenyl($C_1$–$C_6$alkyl)-, phenoxy($C_1$–$C_6$ alkyl)-, heteroaryloxy($C_1$–$C_6$alkyl)-, phenyl($C_1$–$C_6$ alkyl)O($C_1$–$C_6$ alkyl)-, heteroaryl ($C_1$–$C_6$ alkyl)O($C_1$–$C_6$ alkyl)-, phenyl($C_1$–$C_6$ alkyl)S ($C_1$–$C_6$ alkyl)-, or heteroaryl($C_1$–$C_6$ alkyl)S($C_1$–$C_6$ alkyl)- group, any one of which may be optionally substituted by $C_1$–$C_6$ alkyl, $C_1$–$C_6$ alkoxy, halo, cyano (—CN), phenyl, substituted phenyl or heteroaryl.

R₃ is the characterising group of a natural or non-natural a amino acid in which any functional groups may be protected;

R₄ hydrogen, $C_1$–$C_6$ alkyl, phenyl($C_1$–$C_6$ alkyl) or heterocyclyl($C_1$–$C_6$ alkyl);

R₅ is hydrogen or a $C_1$–$C_6$ alkyl group;

or (when R₅ is hydrogen) R₃ and R₄ taken together with the carbon atoms to which they are attached form a 2-hydroxycyclohexyl or $C_6$ sugar (hexose) ring;

or R₄ and R₅ taken together with the carbon atom to which they are attached form a 5 or 6-membered carbocyclic or heterocyclic ring;

or a pharmaceutically acceptable salt, hydrate or solvate thereof.

The term "cycloalkyl" as used herein means a saturated alicyclic ring having from 3–8 carbon atoms and includes, for example, cyclohexyl, cyclooctyl, cycloheptyl, cyclopentyl, cyclobutyl, and cyclopropyl.

The term "cycloalkenyl" as used herein means an unsaturated alicyclic ring having from 5–8 carbon atoms and includes, for example, cyclohexenyl, cyclooctenyl, cycloheptenyl, and cyclopentenyl. The ring may contain more than one double bond.

The unqualified term "heterocyclic" or "heterocyclyl" as used herein means (i) a 3–8 membered heterocyclic ring containing one or more heteroatoms selected from S, N and O, and optionally fused to a benzene ring, including for example, pyrrolyl, furyl, thienyl, imidazolyl, oxazolyl, thiazolyl, thiadiazolyl, pyrazolyl, pyridinyl, pyrrolidinyl, pyrimidinyl, morpholinyl, piperazinyl, indolyl, benzimidazolyl, maleimido, succinimido, phthalimido, 1,2-dimethyl-3,5-dioxo-1,2,4-triazolidin-4-yl, 3-methyl-2,5-dioxo-1-imidazolidinyl and 3,4,4-trimethyl-2,5-dioxo-1-imidazolidinyl, or (ii) a naphththalimido (ie 1,3-dihydro-1,3-dioxo-2H-benz[f]isoindol-2-yl), 1,3-dihydro-1-oxo-2H-benz[f]isoindol-2-yl, 1,3-dihydro-1,3-dioxo-2H-pyrrolo[3,4-b]quinolin-2-yl, or 2,3-dihydro-1,3-dioxo-1H-benz[d,e]isoquinolin-2-yl group.

The term "non-aromatic heterocyclic ring" means a 5–7 membered heterocyclic ring containing one, two or three heteroatoms selected from S, N and O in which at least two adjoining atoms are saturated. Examples include morpholinyl, thiomorpholinyl, dihydrofuranyl, tetrahydrothienyl, dihydrothienyl, piperidinyl, pyrrolidinyl, pyrrolinyl, dioxolanyl, oxathiolanyl, imidazolinyl, imidazolidinyl, pyrazolinyl, pyrazolidinyl, pyranyl, dioxanyl, dithianyl, oxathianyl, and piperazinyl.

The term "heteroaryl" means a 5–7 membered aromatic heterocyclic ring containing one or more heteroatoms. Illustrative of such rings are thienyl, furyl, pyrrolyl, imidazolyl, thiazolyl, pyrazolyl, isoxazolyl, isothiazolyl, trizolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with a phenyl group or up to four substituents, each of which independently may be ($C_1$–$C_6$) alkoxy, hydroxy, mercapto, ($C_1$–$C_6$)alkylthio, amino, halo (including fluoro, chloro, bromo and iodo), cyano, trifluoromethyl, nitro, —COHO, —CONH₂, —CONHR$^A$ or —CONR$^A$R$^A$ wherein R$^A$ is a ($C_1$–$C_8$)alkyl group or the residue of a natural alpha-amino acid.

The term "side chain of a natural or non-natural alpha-amino acid" means the group R in a natural or non-natural amino acid of formula NH₂—CH(R)—COHO.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid and thyroxine.

Natural alpha-amino acids which contain functional substituents, for example amino, carboxyl, hydroxy, mercapto, guanidinyl, imidazolyl or indoxyl groups in their characteristic side chains include arginine, lysine, glutamic acid, aspartic acid, tryptophan, histidine, serine, threonine, tyrosine, and cysteine. When R₃ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$–$C_6$ alkyl ester), amino groups may be converted to amides (for example as a NHCOC$_1$–$C_6$ alkyl amide) or carbamates (for example as an NHC(=O)OC$_1$–$C_6$ alkyl or NHC(=O)OCH₂Ph carbamate), hydroxyl groups may be converted to ethers (for example an OC$_1$–$C_6$ alkyl or a O($C_1$–$C_6$ alkyl)phenyl ether) or esters (for example a OC(=O)C$_1$–$C_6$ alkyl ester) and thiol groups may be converted to thioethers (for example a tert-butyl or benzyl thioether) or thioesters (for example a SC(=O)C$_1$–$C_6$ alkyl thioester).

Examples of side chains of non-natural alpha amino acids include those referred to below in the discussion of suitable R₃ groups for use in compounds of the present invention.

Salts of the compounds of the invention include physiologically acceptable acid addition salts for example hydrochlorides, hydrobromides, sulphates, methane sulphonates, p-toluenesulfonates, phosphates, acetates, citrates, succinates, lactates, tartrates, fumarates and maleates. Salts may also be formed with bases, for example sodium, potassium, magnesium, and calcium salts.

There are several chiral centres in the compounds according to the invention because of the presence of asymmetric carbon atoms. The presence of several asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ and X groups—S,
C atom carrying the $R_2$ group—R,
C atom carrying the $R_3$ group—S, but mixtures in which the above configurations predominate are also contemplated.

In the compounds of the invention the group $R_1$ may be, for example, cyclohexyl, 4-methylcyclohexyl, cyclooctyl, cycloheptyl, cyclopentyl, cyclobutyl, cyclopropyl, tetrahydropyranyl, tetrahydrothien-3-yl, 1,1-dioxo-tetrahydrothien-3-yl, N-acetyl-piperidin-4-yl, N-methylpiperidin4-yl or morpholin-4-yl. Particularly preferred at present are the cases where $R_1$ is cyclopentyl, cyclohexyl and cyclopropyl.

As previously stated, the compounds of the present invention are principally distinguished from the compounds disclosed in the prior patent publications listed above by the identity of the group $R_1$. Accordingly the groups $R_2$ and $R_3$ may include those which have been disclosed in the corresponding positions of compounds disclosed in any of those prior art patent publications listed above. Without limiting the generality of the foregoing, examples of substituents $R_2$ and $R_3$ are given below:

$R_2$ may for example be $C_1$–$C_{12}$ alkyl, $C_3$–$C_6$ alkenyl, phenyl($C_1$–$C_6$ alkyl)- or phenoxy($C_1$–$C_6$ alkyl) optionally substituted in the phenyl ring by halogen, $C_1$–$C_6$ alkyl, $C_1$–$C_6$ alkoxy or phenyl. Specific examples of such groups include iso-butyl, n-pentyl, n-hexyl, n-heptyl, n-octyl, n-nonyl, n-decyl, phenylpropyl, 4-chlorophenylpropyl, 4-methylphenylpropyl, 4-methoxyphenylpropyl, 4-phenyl-phenylpropyl and phenoxybutyl. Presently preferred are compounds in which $R_2$ is iso-butyl, n-octyl, benzyloxypropyl, phenoxybutyl or 4-phenyl-phenylpropyl.

$R_3$ may for example be $C_1$–$C_6$ alkyl, benzyl, 2,- 3-, or 4-hydroxybenzyl, 2,- 3-, or 4-benzyloxybenzyl, 2,- 3-, or 4-$C_1$–$C_6$ alkoxybenzyl, or benzyloxy($C_1$–$C_6$ alkyl)- group; or the characterising group of a natural α amino acid, in which any functional group may be protected, any amino group may be acylated and any carboxyl group present may be amidated; or a group -[Alk]$_n$$R_6$ where Alk is a ($C_1$–$C_6$)alkyl or ($C_2$–$C_6$) alkenyl group optionally interrupted by one or more —O—, or —S—atoms or —N($R_7$)— groups [where $R_7$ is a hydrogen atom or a ($C_1$–$C_6$)alkyl group], n is 0 or 1, and $R_6$ is an optionally substituted cycloalkyl or cycloalkenyl group; or a benzyl group substituted in the phenyl ring by a group of formula—OCH$_2$COR$_8$ where $R_8$ is hydroxyl, amino, ($C_1$–$C_6$)alkoxy, phenyl($C_1$–$C_6$)alkoxy, ($C_1$–$C_6$) alkylamino, di(($C_1$–$C_6$)alkyl)amino, phenyl($C_1$–$C_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid and aspartic acid; or a heterocyclic($C_1$–$C_6$)alkyl group, either being unsubstituted or mono- or di-substituted in the heterocyclic ring with halo, nitro, carboxy, ($C_1$–$C_6$)alkoxy, cyano, ($C_1$–$C_6$)alkanoyl, trifluoromethyl ($C_1$–$C_6$)alkyl, hydroxy, formyl, amino, ($C_1$–$C_6$)alkylamino, di-($C_1$–$C6$)alkylamino, mercapto, ($C_1$–$C_6$)alkylthio, hydroxy($C_1$–$C_6$)alkyl, mercapto($C_1$–$C_6$)alkyl or ($C_1$–$C_6$)alkylphenylmethyl; or a group —CR$_a$R$_b$R$_c$ in which:

each of $R_a$, $R_b$ and $R_c$ is independently hydrogen, ($C_1$–$C_6$)alkyl, ($C_2$–$C_6$)alkenyl, ($C_2$–$C_6$)alkynyl, phenyl($C_1$–$C_6$)alkyl, ($C_3$–$C_8$)cycloalkyl; or $R_c$ is hydrogen, ($C_1$–$C_6$)alkyl, ($C_2$–$C_6$)alkenyl, ($C_2$–$C_6$) alkynyl, phenyl($C_1$–$C_6$)alkyl, or ($C_3$–$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$–$C_6$)alkyl, ($C_2$–$C_6$)alkenyl, ($C_2$–$C_6$)alkynyl, phenyl($C_1$–$C_6$) alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$–$C_4$)perfluoroalkyl, —CH$_2$OH, —CO$_2$($C_1$–$C_6$)alkyl, —O($C_1$–$C_6$)alkyl, —O($C_2$–$C_6$)alkenyl, —S($C_1$–$C_6$)alkyl, —SO ($C_1$–$C_6$)alkyl, —SO$_2$($C_1$–$C_6$) alkyl, —S($C_2$–$C6$) alkenyl, —SO($C_2$–$C_6$)alkenyl, —SO$_2$($C_2$–$C_6$) alkenyl or a group -Q-W wherein Q represents a bond or —O—, —S—, —SO— or —SO$_2$— and W represents a phenyl, phenylalkyl, ($C_3$–$C_8$)cycloalkyl, ($C_3$–$C_8$)cycloalkylalkyl, ($C_4$–$C_8$)cycloalkenyl, ($C_4$–$C_8$)cycloalkenylalkyl, heteroaryl or heteroarylalkyl group, which group W may optionally be substituted by one or more substituents independently selected from, hydroxyl, halogen, —CN, —CO$_2$H, —CO$_2$($C_1$–$C_6$)alkyl, —CONH$_2$, —CONH ($C_1$–$C_6$)alkyl, —CONH($C_1$–$C_6$ alkyl)$_2$, —CHO, —CH$_2$OH, ($C_1$–$C_4$)perfluoroalkyl, —O($C_1$–$C_6$)alkyl, —S($C_1$–$C_6$)alkyl, —SO($C_1$–$C_6$)alkyl, —SO$_2$($C_1$–$C_6$)alkyl, —NO$_2$, —NH$_2$, —NH($C_1$–$C_6$)alkyl, —N(($C_1$–$C_6$)$_2$, —NHCO($C_1$–$C_6$)alkyl, ($C_1$–$C_6$)alkyl, ($C_2$–$C_6$)alkenyl, ($C_2$–$C_6$)alkynyl, ($C_3$–$C_8$) cycloalkyl, ($C_4$–$C_8$)cycloalkenyl, phenyl or benzyl.

Examples of particular $R_3$ groups include benzyl, isobutyl, tert-butyl, 1-fluoro-1-methylethyl, 1-hydroxy-1-methylethyl, 1-methoxy-1-methylethyl, 1-benzylthio-1-methylethyl, 1-methylthio-1-methylethyl and 1-mercapto-1-methylethyl. Presently preferred are compounds in which $R_3$ is t-butyl or 1-mercapto-1-methylethyl.

In the compounds of the invention:

$R_4$ may be, for example, hydrogen, methyl, ethyl, benzyl or pyridylmethyl, and $R_5$ may be, for example hydrogen or methyl. $R_4$ and $R_5$ taken together with the carbon atom to which they are attached may form, for example, a cyclopentyl, cyclohexyl or morpholino ring. Presently preferred are compounds in which $R_4$ and $R_5$ are both hydrogen.

When $R_5$ is hydrogen, $R_3$ and $R_4$ taken together with the carbon atoms to which they are attached may form a 2-hydroxycyclohexyl or a glucose ring.

A preferred subgroup of the compounds of the invention consists of those of formula
(I) wherein $R_1$ is cyclopentyl, cyclohexyl or cyclopropyl;

$R_2$ is iso-butyl, n-octyl, n-nonyl, benzyloxypropyl, phenoxybutyl or 4-phenyl-phenylpropyl;

$R_3$ is t-butyl, 1-mercapto-1-methylethyl or the characterising group of a natural α amino acid, especially histidine; and $R_4$ and $R_5$ are both hydrogen and pharmaceutically acceptable salts, hydrates and solvates thereof.

Specific compounds of the invention include those prepared in the Examples below, as well as:

2S-Cyclopentyl-$N^1$-hydroxy-$N^4$-(1S-hydroxymethyl-2,2-dimethylpropyl)-3R-octyl-succinamide, 3R-(3-Biphenyl-4-yl-propyl)-2S-cyclopentyl-$N^1$-hydroxy-$N^4$-(1 S-hydroxymethyl-2,2-dimethylpropyl)-succinamide, 2S-Cyclopentyl-$N^1$-hydroxy-$N^4$-[2-hydroxy-1S-imidazol-4-ylmethyl)ethyl]-3R-isobutyl succinamide, 3R-(3-Biphenyl-4-yl-propyl)-2S-cyclopentyl-$N^1$-hydroxy-$N^4$-(2-hydroxy-1S-imidazol-4-ylmethyl)-ethyl]-3R-isobutyl succinamide, 2S-Cyclopentyl-$N^1$-hydroxy-$N^4$-[2-hydroxy-1S-(4-hydroxybenzyl)-ethyl]-3R-isobutyl-succinamide, $N^4$-(1S-Benzyl-2-hydroxy-ethyl)-$N^1$-hydroxy-3R-isobutyl-2S-(tetrahydrothiophen-2-yl)-succinamide, $N^4$-(1S-Benzyl-2R-hydroxy-butyl)-3R-(3-Biphenyl-4-yl-propyl)-2S-cyclopentyl-$N^1$-hydroxy-succinamide, $N^4$-(1S-Benzyl-2S-hydroxy-butyl)-3R-(3-Biphenyl-4-yl-propyl)-2S-cyclopentyl-$N^1$-hydroxy-succinamide, 3R-(3-Biphenyl-4-yl-propyl)-2S-cyclopentyl-$N^1$-hydroxy-$N^4$-(1S-hyd roxymethyl-3-methylbutyl)-succinamide, 6-Biphenyl-4-yl-2S-cyclopentyl-3R-(2S-hydroxymethyl)-pyrrolidine-1-carbonyl)-hexanoic acid hydroxyamide, 3R-(3-Biphenyl-4-yl-propyl)-$N^4$-(1S-tert-butyl-2R-hydroxy-butyl)-2S-cyclopentyl-$N^1$-hydroxy-succinamide, 3R-(3-Biphenyl-4-yl-propyl )-$N^4$-(1S-tert-butyl-2S-hydroxy-butyl)-2S-cyclopentyl-$N^1$-hydroxy-succinamide, and pharmaceutically acceptable salts, hydrates and solvates thereof.

Compounds according to the present invention in which X is a hydroxamic acid group —CONHOH may be prepared from corresponding compounds of the invention in which X is a carboxylic acid group —$CO_2H$ or from the corresponding protected hydroxamic acid derivatives. That process, which forms another aspect of the invention, comprises causing an acid of general formula (II)

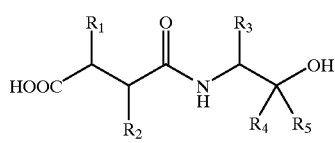

(II)

in which the hydroxy group attached to the C atom carrying the $R_4$ and $R_5$ groups may be protected, or an activated derivative thereof, to react with hydroxylamine, O-protected hydroxylamine, or an N,O-diprotected hydroxylamine, or a salt thereof, $R_1$, $R_2$, $R_3$, $R_4$, and $R_5$ being as defined in general formula (I) except that any substituents in $R_1$, $R_2$, $R_3$, $R_4$, and $R_5$ which are potentially reactive with hydroxylamine, O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, $R_4$, and $R_5$ Conversion of (II) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in method (a) above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in method (a) above include N,O-bis(benzyl)hydroxylamine, N,O-bis(4-methoxybenzyl)hydroxylamine, N-tert-butoxycarbonyl-O-tert-butyidimethylsilylhydroxylamine, N-tert-butoxycarbonyl-O-tetrahydropyranylhydroxylamine, and N,O-bis(tert-butoxycarbonyl)hydroxylamine.

Compounds according to the present invention in which X is a carboxylic acid group —COOH, ie compounds of formula (II) above, may be prepared by a process comprising: coupling an acid of formula (III) or an activated derivative thereof with an amino alcohol of formula (IV)

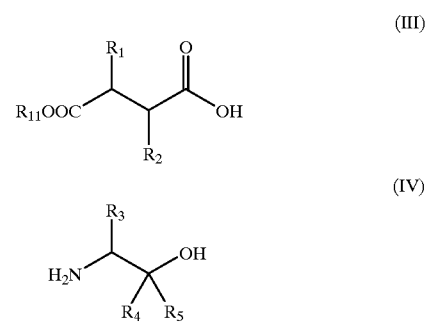

wherein $R_1$, $R_2$, $R_3$, $R_4$, and $R_5$ are as defined in general formula (I) except that any substituents in $R_1$, $R_2$, $R_3$, $R_4$, and $R_5$ which are potentially reactive in the coupling reaction may themselves be protected from such reaction, and $R_{11}$ represents a hydroxy protecting group, and subsequently removing the protecting group $R_{11}$ and any protecting groups from $R_1$, $R_2$, $R_3$, $R_4$, and $R_5$.

Active derivatives of acids (III) include activated esters such as the pentafluorophenyl ester, acid anhydrides and acid halides, eg chlorides. Suitable hydroxy protecting groups may be selected from those known in the art.

Amino alcohols of formula (IV) are either commercially available or are prepared by routine known synthetic methods. Compounds of formula (III) may be prepared by one or more of the following routes:

Route 1: By Ireland-Claisen rearrangement of compounds of formula (V) to products (VI)

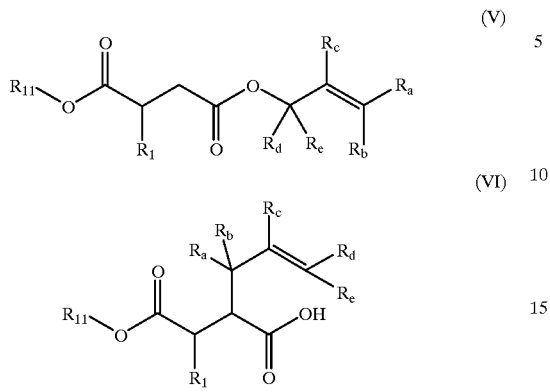

in which formulae $R_1$ and $R_{11}$ have the meanings ascribed to them in formula (III), and $R_a$–$R_e$ are substituents selected so that the partial structure (VII)

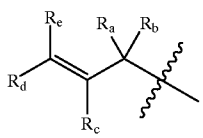

corresponds to the desired $R_2$ substituent in compound (III).

Claisen rearrangement of allyl enol ethers is useful for stereocontrolled carbon-carbon bond formation (for recent reviews see P. Wipf in *Comprehensive Organic Synthesis*, Vol. 5 (Eds.: B. M. Trost, I. Fleming, L. A. Paquette) Pergamon, New York, 1991, p 827; S. Blechert, Synthesis, 1989, 71; F. E. Zeigler, Chem. Rev., 1988, 88, 1423). Among the available methods for effecting this [3,3] sigmatropic rearrangement is the Ireland-Claisen procedure, by which a silyl ketene acetal of an allyl ester can be converted to an α-allyl carboxylic acid. A particularly important aspect of the Ireland Claisen rearrangement is that, through efficient control of ketene acetal geometry, a highly reliable transfer of stereochemistry from starting material to product can be realised (R. E. Ireland, P. Wipf and J. D. Armstrong, *J. Org. Chem.* 1991, 56, 650; ibid 56, 3572).

The rearrangement may be effected in an aprotic solvent such as tetrahydrofuran, by first converting the substituted allyl ester (V) to the enol form, for example by treatment with a strong organic base, such as lithium diisopropylamine, followed by silylation of the enol hydroxy group, using a silylating agent (eg trimethylsilyl chloride, triethylsilyl chloride, tripropylsilyl chloride, tert-butyidimethylsilyl chloride, or tert-butyidiphenylsilyl chloride). The resultant silyl ketene acetal then undergoes the desired rearrangement to produce the readily hydrolysable silyl ester of compound (V). In the foregoing procedure, enolisation and silylation are preferably effected at low temperature, eg –70° C. or lower, and the rearrangement may be induced by raising the temperature, eg to about 4° C. to 55° C.

The allylic double bond of product (VI) of the rearrangement of (V) may be reduced, for example by catalytic hydrogenation, to form compounds (VIA), in which $R_1$ and $R_{11}$ have the meanings ascribed to them in formula (III), and $R_a$–$R_e$ are substituents selected so that the partial structure (VIIA)

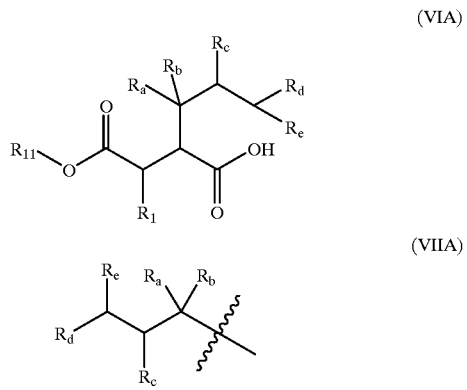

corresponds to the desired $R_2$ substituent in compound (III).

This Route 1 to compounds (III) involving rearrangement of compounds (IV) to (V), possibly followed by reduction of the allylic double bond, represents a novel application of the Ireland-Claisen rearrangement to the synthesis of 2,3-disubstituted succinates.

Route 2: By Ireland-Claisen rearrangement (as discussed above in relation to Route 1 of compounds of formula (VIII) to products (IX)

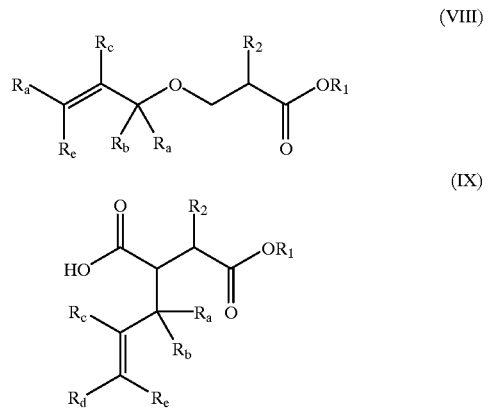

in which formulae $R_2$ and $R_{11}$ have the meanings ascribed to them in formula (III), and $R_a$–$R_e$ are substituents selected so that the partial structure (VII)

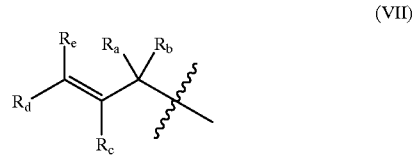

corresponds to the desired $R_1$ substituent in compound (III). In this instance, the groups $R_a$ and $R_d$ are linked to form part of the desired alicyclic or heterocyclic ring, $R_1$. Again the double bond in partial structure (VI) of product (IX) may be reduced to form compounds (IXA)

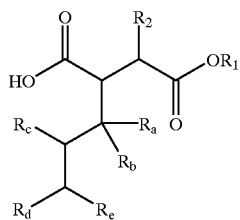

(IXA)

in which $R_1$ and $R_{11}$ have the meanings ascribed to them in formula (III), and $R_a$–$R_e$ are substituents selected so that the partial structure (VIIA) corresponds to the desired $R_1$ substituent in compound (III).

This Route 2 to compounds (III) involving rearrangement of compounds (VIII) to (IX), possibly followed by reduction of the allylic double bond, represents a novel application of the Ireland-Claisen rearrangement to the synthesis of 2,3-disubstituted succinates.

Route 3: By alkylation of a succinate of formula (X) with an alkylating agent $R_1$-L, or by alkylation of a succinate of formula (XA) with an alkylating agent $R_2$-L, where L is a suitable leaving group such as chloride, bromide, iodide, triflate or mesylate,

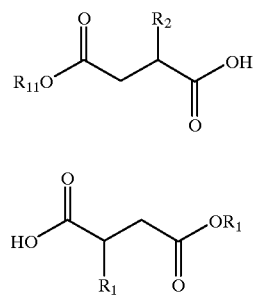

(X)

(XA)

wherein $R_1$, $R_2$, and $R_{11}$ are as defined in relation to formula (III) above.

Succinates of formula (V), (VI), (VIII), (IX), (X) and (XA) insofar as they are not known from the literature can be prepared, in homochiral form if desired, by methods known in the art. In the special case where $R_1$ is a nitrogen-containing heterocycle linked through a nitrogen atom, compounds of formula (III) may be prepared according to Route 1 from a suitably protected aspartic acid derivative (XI)

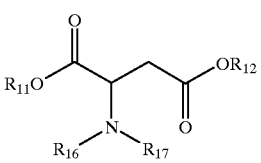

(XI)

wherein $R_{11}$ and $R_{12}$ are carboxyl protecting groups, and $R_{16}$ and $R_{17}$ taken together with the nitrogen atom to which they are attached form the desired nitrogen containing non-aromatic heterocyclic group $R_1$.

As mentioned above, compounds of formula (I) are useful in human or veterinary medicine since they are active as inhibitors of MMPs Accordingly in another aspect, this invention concerns:
(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and
(ii) a compound as defined with respect to formula (I) for use in human or veterinary medicine, particularly in the management (by which is meant treatment or prophylaxis) of diseases or conditions mediated by MMPS; and
(iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases as well as neuroinflammatory disorders, including those involving myelin degradation, for example multiple sclerosis. Diseases or conditions mediated by TNF include inflammation, fever, cardiovascular effects, haemorrhage, coagulation and acute phase response, cachexia and anorexia, acute infections, shock states, graft versus host reactions and autoimmune disease.

In a further aspect of the invention there is provided a pharmaceutical or veterinary composition comprising a compound of formula (I) together with a pharmaceutically or veterinarily acceptable excipient or carrier. In view of the water-solubility, and oral bioavailability advantanges of compounds in accordance with the invention, a further aspect of the invention comprises a pharmaceutical or veterinary composition comprising a compound of formula (I) together with a pharmaceutically or veterinarily acceptable excipient or carrier, characterised in that the composition is adapted for oral administration.

One or more compounds of general formula (I) may be present in the composition together with one or more excipient or carrier.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite os disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples which follow serve to illustrate embodiments of the invention.

The following abbreviations have been used throughout:

| | |
|---|---|
| DMAP | 4-Dimethyl-aminopyridine |
| DMF | N,N-Dimethylformamide |
| EDC | N-Ethyl-N'-(3-dimethylaminopropyl)carbodiimide hydrochloride |
| HOBt | 1-Hydroxybenzotriazole |
| NMR | Nuclear magnetic resonance |
| NMM | N-methylmorpholine |
| NaHMDS | Sodium bis(trimethylsilyl)amide |
| TESCl | Chlorotriethylsilane |
| TFA | Trifluoroacetic acid |
| THF | Tetrahydrofuran |
| TLC | Thin layer chromatography |

$^1$H and $^{13}$C NMR spectra were recorded using a Bruker AC 250E spectrometer at 250.1 and 62.9 MHz, respectively. Elemental microanalyses were performed by either CHN Analysis Ltd., Alpha House, Countesthorpe Road, South Wigston, Leicester LE8 2PJ, UK, or MEDAC Ltd., Dept. of Chemistry, Brunel University, Uxbridge, Middlesex UB8 3PH, UK.

EXAMPLE 1

2S-Cyclopentyl-3R-(1S-hydroxymethyl-2-phenyl-ethylcarbamoyl)-5-methyl-hexanoic acid

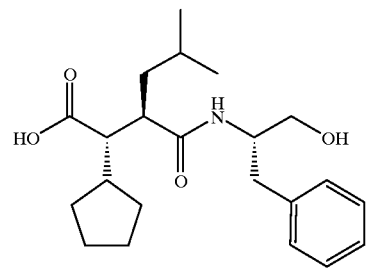

The synthetic route to the title compound is outlined in Scheme 1 and described in detail below.

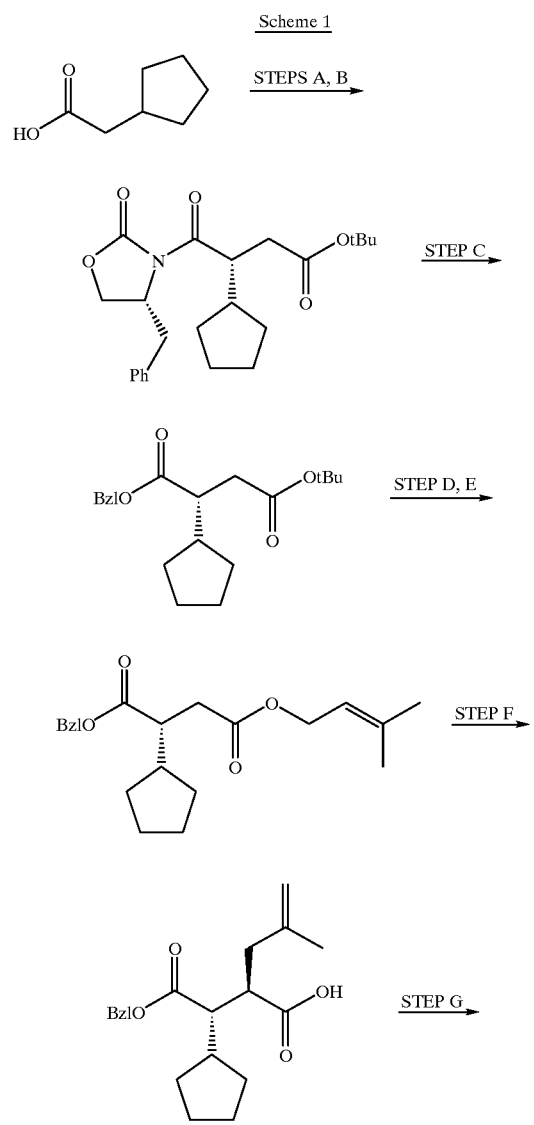

-continued

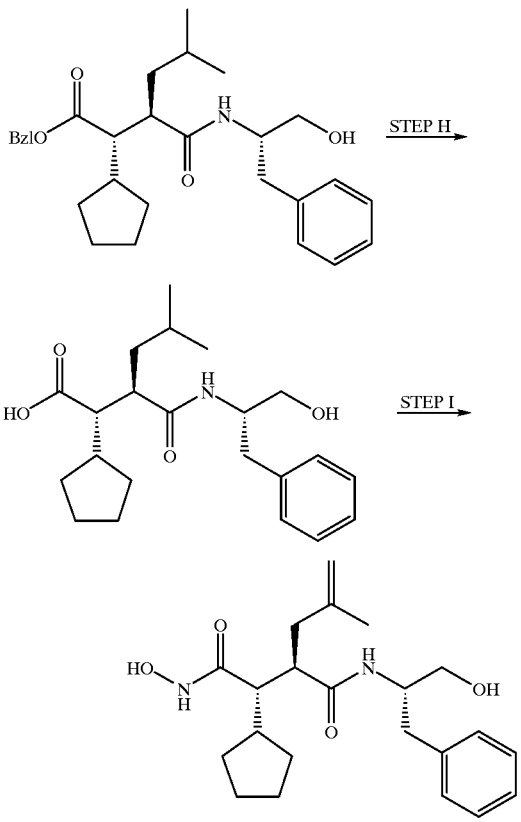

Reagents and conditions: (a) $^t$BuCOCl, Et$_3$N, (R)-Evans auxiliary, THF -78° C.; (b) NaN(SiMe$_3$)$_2$, BrCH$_2$CO$_2^t$Bu, THF, -78° C.; (c) BzlOLi, THF, -5° C.; (d) TFA, CH$_2$Cl$_2$, 4° C., overnight; (e) CH$_2$=C(Me)CH$_2$OH, EDC, DMAP, CH$_2$Cl$_2$; (f) LDA, THF, -78° C. then Et$_3$SiCl, 55° C. overnight; (g) phenylalaninol, HOBt, EDC, DMF, overnight; (h) H$_2$, 10% Pd/C, methanol; (i) HOBt, EDC, DMF then HONH$_2$OH•HCl/NMM.

Step A

4R-Benzyl-3-cyclopentylacetyl-oxazolidin-2-one

Cyclopentyl acetic acid (59 ml, 470.4 mmol) was taken up in dry THF (1 l) and cooled to -78° C. under argon. Pivaloyl chloride (58 ml, 470.4 mmol) and triethylamine (85 ml, 611.5 mmol) were added and the reaction mixture stirred for 15 min at -78° C. and then warmed to 0° C. and stirred for 40 min before cooling back to -78° C. In a separate flask, 4R-benzyl-oxazolidin-2-one (100 g, 564.5 mmol) was dissolved in dry THF (1 l) and the solution was cooled to -78° C. under argon. To this stirred solution was added 2.5 M n-butyllithium in hexanes (226 ml, 565 mmol). After the addition was complete the resulting solution was cannulated into the former reaction flask and the mixture was stirred for a further 15 minutes at -78° C. before warming to room temperature and stirring overnight. The reaction was quenched by addition of 1M potassium hydrogen carbonate solution (600 ml). The solvents were removed under reduced pressure and the residue was extracted into ethyl acetate (×3). The combined ethyl acetate extracts were washed with brine, dried over magnesium sulphate and filtered. The solution was concentrated under reduced pressure to give a yellow oil which crystallised on standing (139.8 g, including residual solvent). $^1$H-NMR; δ (CDCl$_3$), 7.37–7.20 (5H, m), 4.69 (1H, m), 4.23–4.12 (2H, m, 3.30 (1H, dd, J=13.3, 3.3 Hz), 3.04 (1H, dd, J=16.6, 7.1 Hz), 2.91 (1H, dd, J=16.6, 7.1 Hz), 2.77 (1H, dd, J=13.3, 3.3 Hz), 2.34 (1H, m), 1.94–1.83 (2H, m), 1.69–1.52 (4H, m) and 1.30–1.14 (2H, m).

Step B 4-(4R-Benzyl-2-oxo-oxazolidin-3-yl-3R-cyclopentyl-4-oxo-butyric acid tert-butyl ester 4R-Benzyl-3-cyclopentylacetyl-oxazolidin-2-one (Step A) (135 g, 469.8 mmol) was dissolved in dry THF (2 l) and the solution was cooled to -78° C. under argon. To this cooled solution was added a 1.0 M solution NaHMDS in THF (705 ml, 705 mmol). The resulting mixture was stirred for a further 1 hour at -78° C., tert-butyl bromoacetate (114 ml, 705 mmol) was added and the reaction mixture was then stored in the freezer (-20° C.) for 48 hours. A saturated solution of ammonium chloride (500 ml) was added and the solvent was removed under reduced pressure. The resulting aqueous residue was extracted into ethyl acetate (×3). The ethyl acetate extracts were combined, washed with brine, dried over magnesium sulphate, filtered and evaporated under reduced pressure to give a white solid. Recrystallisation from ethyl acetate/hexane gave the desired product (98.5 g, 52%).

$^1$H-NMR; δ (CDCl$_3$), 7.38–7.23 (5H, m), 4.67 (1H, m), 4.25 (1H, m), 4.15–4.13 (2H, m), 3.38 (1H, dd, J=13.5, 3.2 Hz), 2.86 (1H, dd, J=16.8, 11.2 Hz), 2.73 (1H, dd, J=13.5, 11.2 Hz), 2.53 (1H, dd, J=16.8, 3.2 Hz), 2.00 (1H, m), 1.83 –1.44 (6H, m), 1.42 (9H, s) and 1.41–1.17 (2H, m).

Step C

2R-Cyclopentylsuccinic acid 1-benzyl ester 4-tert-butyl ester

Benzyl alcohol (40 ml, 386.1 mmol) was dissolved in dry THF (800 ml) and the solution was placed under argon and cooled to -5° C. using a methanol/ice bath. To this stirred solution was added 2.5M n-butyllithium in hexanes (116 ml, 290 mmol) slowly over a period of 45 minutes, so that the temperature remained below 0° C. throughout the addition. After the addition was complete, the reaction mixture was stirred for a further 40 minutes at -5° C. Separately, a solution of 4-(4R-benzyl-2-oxo-oxazolidin-3-yl-3R-cyclopentyl-4-oxo-butyric acid tert-butyl ester (Step B) (77.9 g, 193 mmol) in dry THF (400 ml) was placed under argon, cooled to -5° C. and cannulated into the former reaction flask and the mixture was stirred for a further 15 minutes at -5° C., before warming to room temperature and stirring overnight. The reaction was quenched with saturated ammonium chloride solution (450 ml), the solvents were removed under reduced pressure and the residue was extracted with ethyl acetate (×2). The combined organic extracts were washed with brine, dried over anhydrous magnesium sulphate and filtered. The filtrate was concentrated under reduced pressure to give a clear oil which was purified by column chromatography (silica gel, 20% ethyl acetate in hexane) to give the title compound as a clear oil (40.9 g, 86%). $^1$H-NMR; δ (CDCl$_3$), 7.45–7.29 (5H, m), 5.19 (2H, m), 2.92–2.73 (2H, m), 2.49 (1H, m), 2.01 (1H, m), 1.84–1.49 (6H, m), 1.41 (9H, s) and 1.38–1.19 (2H, m).

Step D

2R-Cyclopentylsuccinic acid 1-benzyl ester

2R-Cyclopentyl-succinic acid 1-benzyl ester 4-tert-butyl ester (Step C) (36.43 g, 109.6 mmol) was dissolved in dichloromethane (300 ml) and TFA (200 ml) and the resulting solution was stored at 4° C. overnight. The solvents were removed under reduced pressure and the residue was azeotroped with toluene (×3) to give the product as a brown oil (30.30 g, quant). $^1$H-NMR; δ (CDCl$_3$), 11.50 (1H, br s), 7.45–7.29 (5H, m), 5.19 (2H, m), 2.94–2.74 (2H, m), 2.60 (1H, m), 2.07 (1H, m), 1.84–1.52 (6H, m) and 1.38–1.22 (2H, m).

Step E

2R-Cyclopentylsuccinic acid 1-benzyl ester 4-(2-methylallyl) ester

2R-Cyclopentylsuccinic acid 1-benzyl ester (Step D) (23.5 g, 85 mmol) was dissolved in dichloromethane (200 ml) and EDC (19.5 g, 102 mmol), DMAP (200 mg, catalytic) and 2-methyl 2-propen-1-ol (7.5 ml, 89 mmol) were added. The resulting mixture was stirred at room temperature overnight. The solvent was removed under reduced pressure and the residue was dissolved in ethyl acetate. The organic solution was washed successively with 1M hydrochloric acid, 1M sodium carbonate and brine, then dried over magnesium sulphate and filtered. The solvent was removed under reduced pressure to leave an oil which was purified by column chromatography (silica gel, 20% ethyl acetate in hexane) to give the title compound as a colourless oil (21.4 g, 76%). $^1$H-NMR; δ (CDCl$_3$), 7.36–7.27 (5H, m), 5.19–5.07 (2H, m), 4.93 (2H, d, J=5.4 Hz), 4.46 (2H, s), 2.89–2.71 (2H,m), 2.58 (1H, m), 2.03 (1H, m), 1.73 (3H, s), 1.64–1.49 (6H, m), 1.36–1.16 (2H, m).

Step F

2S-Cyclopentyl-3R-(2-methylallyl)succinic acid 4-benzyl ester

Diisopropylamine (29.3 ml, 209 mmol) was taken up in dry THF (700 ml) and cooled to −78° C. under argon before addition of a 2.3 M solution of butyllithium in hexanes (83.3 ml, 192 mmol). The reaction was allowed to warm briefly to −30° C. and then cooled back to −78° C. 2R-Cyclopentylsuccinic acid 1-benzyl ester 4-(2-methylallyl) ester (Step E) (57.54 g, 174 mmol) was added and the resulting mixture was stirred for 45 minutes. TESCl (32.2 ml, 192 mmol) was added and, after stirring for a further 30 minutes at −78° C., the reaction mixture was warmed to 55° C. and stirred overnight. The reaction was quenched by addition of 1M hydrochloric acid in methanol and the solvents were removed under reduced pressure. The residue was dissolved in ethyl acetate and washed successively with 1M hydrochloric acid and brine, dried over magnesium sulphate, filtered and concentrated under reduced pressure to give a brown oil. Purification by column chromatography (silica gel, 10% methanol in dichloromethane) afforded the title compound as a yellow oil (24.74 g, 43%). $^1$H-NMR; δ (CDCl$_3$), 7.36 (5H, m), 5.12 (2H, m), 4.71 (2H, d, J=11.2 Hz), 2.94 (1H, m), 2.74 (1H, dd, J=8.3, 8.4 Hz), 2.33 (1H, m), 2.14 (2H, m), 1.89–1.45 (6H, br m), 1.68 (3H, s) and 1.28 (2H, br m)

Step G

2S-Cyclopentyl-3R-(1S-hydroxymethyl-2-phenyl-ethylcarbamoyl)-5-methyl-hex-5-enoic acid benzyl ester 2S-Cyclopentyl-3R-(2-methylallyl)succinic acid 4-benzyl ester (Step F) (519 mg, 1.57 mmol) was dissolved in DMF (20 ml) and to the solution were added phenylalaninol (262 mg, 1.73 mmol), HOBt (255 mg, 1.89 mmol) and EDC (332 mg, 1.73 mmol). The mixture was stirred overnight at room temperature. The solvent was removed under reduced pressure and the residue was dissolved in ethyl acetate (50 ml). The organic solution was washed successively with 1M hydrochloric acid and 1M sodium carbonate solution, dried over magnesium sulphate and filtered. The residue was purified by column chromatography (silica gel, 2% methanol in dichloromethane) to afford the title compound as a white solid (533 mg, 73%). $^1$H-NMR; δ (CDCl$_3$): 7.41 (5H, m), 7.27 (5H, m), 5.82 (1H, d, J=7.3 Hz), 5.20 (1H, dd, J=17.4 Hz), 5.15 (1H, dd, J=17.4Hz), 4.76 (2H, d, J=18.0 Hz), 4.25 (1H, m), 3.69 (1H, m), 3.59 (1H, dd, J=11.1, 11.1 Hz), 2.97 (1H, dd, J=6.4, 14.0 Hz), 2.81 (1H, m), 2.61 (1H, m), 2.42 (1H, dd, J=13.5, 13.4 Hz), 2.01 (1H, m), 1.83 (1H, m), 1.71 (3H, s) and 1.67–1.16 (10H, br m).

Step H

2S-Cyclopentyl-3R-(1S-hydroxymethyl-2-phenyl-ethylcarbamoyl)-5-methyl-hexanoic acid 2S-Cyclopentyl-3R-(1S-hydroxymethyl-2-phenyl-ethylcarbamoyl)-5-methyl-hex-5-enoic acid benzyl ester (Step G) (533 mg, 1.15 mmol) was dissolved in methanol (35 ml) and the solution was placed under a blanket of argon. 10% Palladium on charcoal (300 mg) was added and the suspension was placed under an atmosphere of hydrogen and stirred overnight. TLC showed that all the starting material had been consumed. The system was purged with argon and the catalyst was removed by filtration. Solvent was evaporated to give the desired product as a white solid (399 mg, 92%). $^1$H-NMR; δ (CDCl$_3$/CD$_3$OD), 7.16 (5H, m), 4.08 (1H, m), 3.49 (2H, d, J=4.78 Hz), 2.86 (1H, dd, J=6.6, 13.9 Hz), 2.71 (1H, dd, J=8.3, 13.9 Hz), 2.36 (2H, m), 1.74 (1H, m), 1.68–1.00 (11H, br m) and 0.76 (6H, d, J=7.3 Hz).

EXAMPLE 2

3R-(1S-Benzyl-2-hydroxy-ethylcarbamoyl)-6-biphenyl-4-yl-propyl-2S-cyclopentyl-hexanoic acid

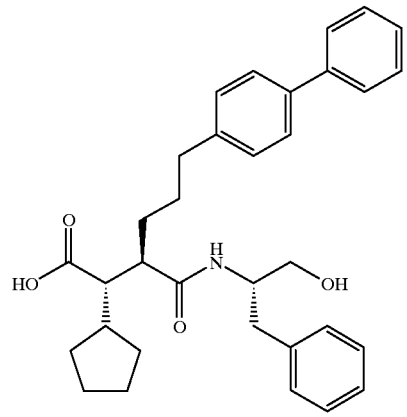

The synthetic route to the title compound is outlined in Scheme 2 and described in detail below. The starting material 2R-Allyl-3S-cyclopentyl-succinic acid 4-benzyl ester was prepared by analogy with Example 1, substituting allyl alcohol for 2-methyl 2-propen-1-ol in Step E.

Scheme 2

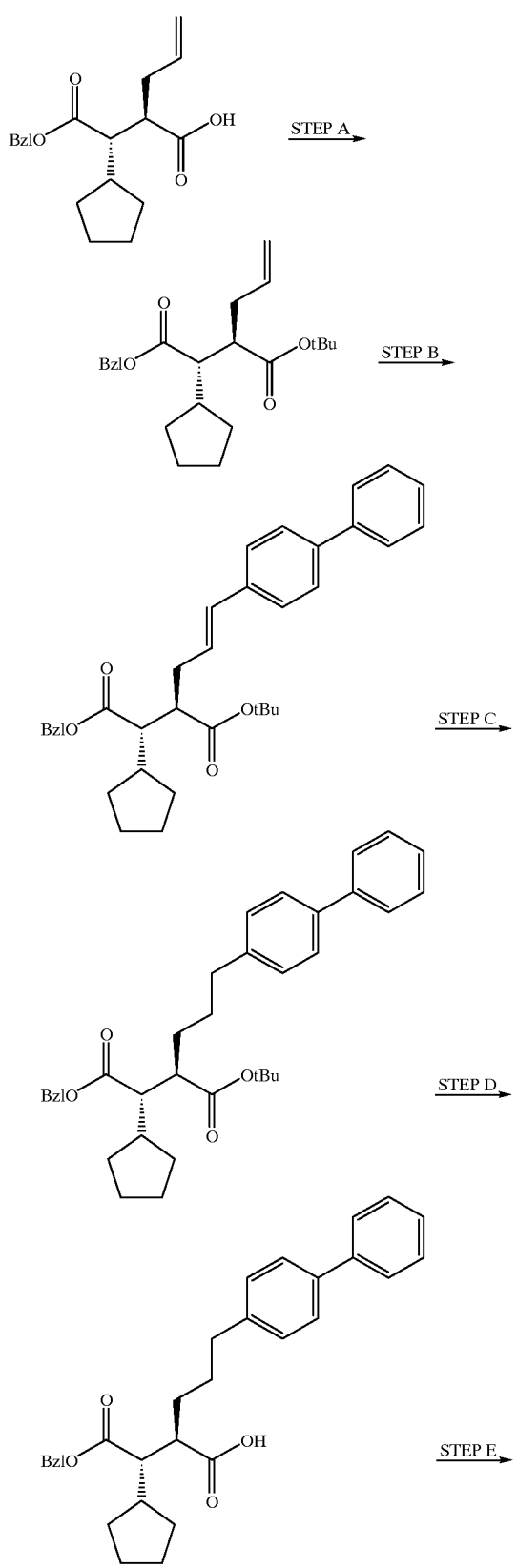

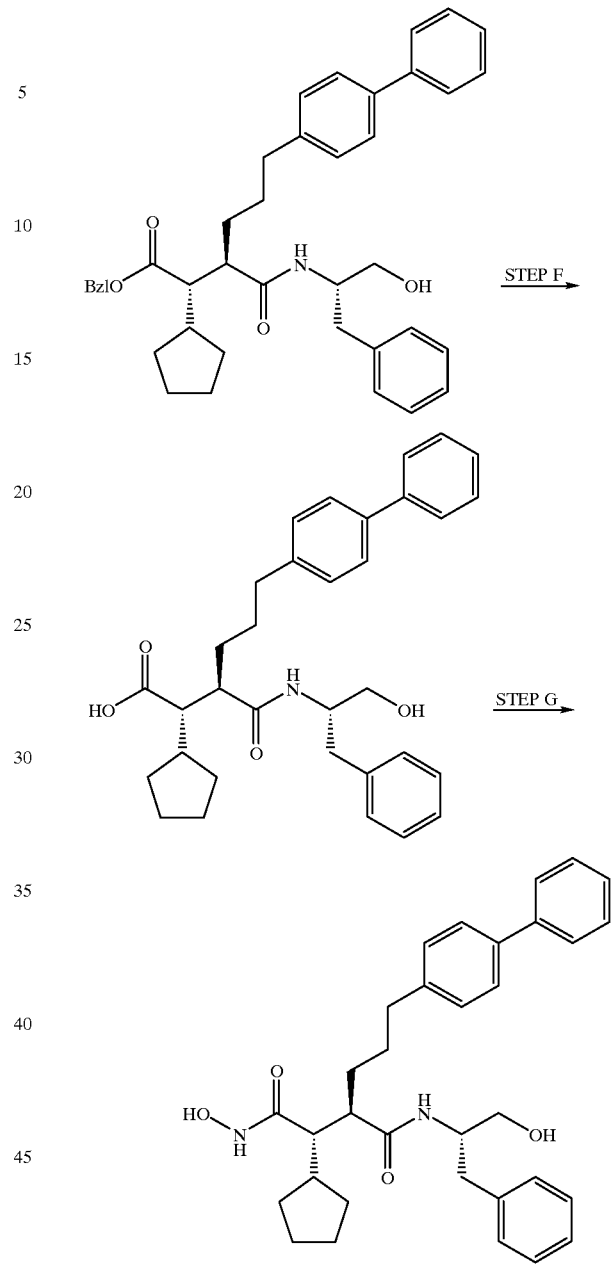

Reagents and conditions: (a) Isobutene, H$_2$SO$_4$, -78 to 0° C.; (b) 4'-Bromobiphenyl, Pd(OAc)$_2$, P(o-Tolyl)$_3$, Et$_3$N, CH$_3$CN, 80° C.; (c) H$_2$NOH•HCl, KOH, DMF/EtOAc, 100° C., 4 hours; (d) TFA, CH$_2$Cl$_2$, 4° C. overnight; (e) phenylalaninol, HOBt, EDC, DMF, overnight; (f) H$_2$, 10% Pd/C, methanol; (i) HOBt, EDC, DMF then HONH$_2$OH•HCl/NMM.

Step A

2S-Allyl-3S-cyclopentyl-succinic acid 4-benzyl ester 1-tert-butyl ester

2S-Allyl-3S-cyclopentyl-succinic acid 4-benzyl ester (9.46 g, 29.9 mmol) was dissolved in dichloromethane (45 ml) in a pressure bottle and cooled to −78° C. with stirring before addition concentrated sulfuric acid (3 ml). Isobuylene was condensed into the reaction mixture until the volume of solution had approximately doubled and the reaction vessel was sealed. The solution was allowed to warm to room temperature and stirred overnight. After cooling to −78° C. the vessel was opened and then allowed to warm back to room temperature. The solution was poured into 1M sodium carbonate solution (200 ml) with stirring, and the dichloromethane was evaporated. The remaining aqueous phase was extracted with ethyl acetate (3×50 ml) and the combined organic extracts were dried over anhydrous magnesium sulphate, filtered and evaporated to give the title compound as an orange oil (10.72 g, 96%) which was used without further purification. $^1$H-NMR; δ (CDCl$_3$), 7.36 (5H, s), 5.75 (1H, m) 5.14, 5.07 (2H, AB system, J$_{AB}$=12.2 Hz), 5.03 (2H, m), 2.72 (2H, m), 2.38–2.08 (3H, m), 1.76 –1.15 (8H, m) and 1.42 (9H, s).

Step B 2S-(3-Biphenyl-4-yl-allyl )-3S-cyclopentyl-succinic acid 4-benzyl ester 1-tert butyl ester 2S-Allyl-3S-cyclopentyl-succinic acid 4-benzyl ester 1-tert-butyl ester (8.96 g, 24 mmol) was dissolved in acetonitrile (48 ml) and the solution was placed under a blanket of argon in a pressure bottle. 4'-Bromobiphenyl (11. 18 g, 48 mmol), tri-o-tolyl-phosphine (1.46 g, 4.8 mmol) and triethylamine (6.6 ml, 48 mmol) were added, followed by palladium (II) acetate (540 mg, 2.4 mmol). The vessel was sealed and heated at 80° C. for 3 hours. The reaction was cooled to room temperature, diluted with ethyl acetate (50 ml) and filtered. The filtrate was further diluted with ethyl acetate and the solution was washed successively with 1M hydrochloric acid, water and brine, dried over anhydrous magnesium sulphate, filtered and evaporated. The residue was purified by column chromatography (silica gel, 9% ethyl acetate in hexane) to give the title compound as a white solid (8.84 g, 70%). $^1$H-NMR; δ (CDCl$_3$), 7.60 (2H, d, J=7.1 Hz), 7.54 (2H, d, J=8.2 Hz), 7.46 (2H, dd, J=7.1, 7.1 Hz), 7.37 (8H, m), 6.42 (1H, d, J=15.8 Hz), 6.20 (1H, m), 5.18 (1H, d, J=12.4 Hz), 5.10 (1H, d, J=12.4 Hz), 2.80 (2H, m), 2.60–2.35 (2H, m), 2.11 (1H, m), 1.42 (9H, s) and 1.80–1.29 (8H, m). $^{13}$C-NMR; δ (CDCl$_3$),173.3, 172.9, 140.6, 139.7, 136.3, 128.8, 128.6, 128.4, 127.7, 127.0, 126.8, 126.5, 126.4, 80.8, 66.1, 51.7, 48.4, 41.3, 33.9, 30.6, 29.2, 27.9, 24.9 and 24.6.

Step C 2R-(3-Biphenyl-4-yl-propyl)-3S-cyclopentyl-succinic acid 4-benzyl ester 1-tert butyl ester Hydroxylamine hydrochloride (89.8 g, 1.29 mol) was dissolved in DMF (250 ml) and the solution was placed under an argon blanket. Crushed potassium hydroxide (85.3 g, 1.52 mol) was added slowly with stirring and cooling in an ice bath. After the addition was complete, the mixture was stirred for a further 15 minutes then filtered. The filtrate was cooled to 0° C. and ethyl acetate (50 ml) was added. The resulting solution was added dropwise to a flask containing 2S-(3-Biphenyl-4-yl-allyl)-3S-cyclopentyl-succinic acid 4-benzyl ester 1-tert butyl ester (8.84 g, 16.8 mmol) under argon. The resulting mixture was heated at 100° C. for 4 hours, cooled to room temperature, diluted with water and extracted twice with ethyl acetate. The combined organic extracts were washed successively with water, 1M hydrochloric acid and brine, dried over anhydrous magnesium sulphate, filtered and evaporated. The residue was redissolved in ethyl acetate and washed several times with water to ensure removal of DMF. The organic solution was dried and concentrated to an oil (7.97 g) containing the desired product along with 8% of the starting alkene, which was used without further purification. $^1$H-NMR; δ (CDCl$_3$), 7.56 (2H, d, J=7.2 Hz), 7.49 (2H, d, J=8.1 Hz), 7.43 (2H, dd, J=7.0, 7.0 Hz), 7.35 (6H, m), 7.19 (2H, d, J=8.1 Hz), 5.11, 5.07 (2H, AB system, J$_{AB}$=12.6 Hz), 2.74–2.57 (4H, m), 2.06 (1H, m), 1.72–1.27 (12H, m) and 1.43 (9H, s).

3R-(1S-Benzyl-2-hydroxy-ethylcarbamoyl)-6-biphenyl4-yl-propyl-2S-cyclopentyl-hexanoic acid was obtained in three steps from 2R-(3-Biphenyl-4-yl-propyl)-3S-cyclopentyl-succinic acid 4-benzyl ester 1-tert-butyl ester by analogy with Example 1:

Step D 2R-(3-Biphenyl-4-yl-propyl)-3S-cyclopentyl-succinic acid 4-benzyl ester TFA acidolysis of 2R-(3-Biphenyl-4-yl-propyl)-3S-cyclopentyl-succinic acid 4-benzyl ester 1-tert-butyl ester (570 mg, 1.08 mmol) provided the title compound was isolated as a colourless oil (510 mg, quant.). $^1$H-NMR; δ (CDCl$_3$), 7.59 (2H, d, J=7.2 Hz), 7.53 (2H, d, J=8.1 Hz), 7.46 (2H, dd, J=7.1, 7.1 Hz), 7.38 (6H, m), 7.23 (2H, d, J=8.1 Hz), 5.15 (2H, s), 2.81 (2H, m), 2.61 (2H, m), 2.12 (1H, m) and 1.79–1.40 (12H, m).

Step E 3R-(1S-Benzyl-2-hydroxy-ethylcarbamoyl)-6-biphenyl-4-yl-propyl-2S-cyclopentyl-hexanoic acid benzyl ester Activated ester coupling of 2R-(3-Biphenyl-4-yl-propyl)-3S-cyclopentyl-succinic acid 4-benzyl ester (670 mg, 1.42 mmol) with phenylalaninol provided the title compound as a white foam after column chromatography (230 mg, 27%). $^1$H-NMR; δ (CDCl$_3$), 7.60–7.14 (14H, m), 7.33 (5H, s), 5.85 (1H, d, J=7.3 Hz), 5.06 (2H, s), 4.20 (1H, m), 3.62 (2H, m), 2.88 (2H, m), 2.76 (3H, m), 2.51 (2H, m), 2.33 (1H, m) and 1.79–1.22 (13H, m).

Step F 3R-(1S-Benzyl-2-hydroxy-ethylcarbamoyl)-6-biphenyl4-yl-propyl-2S-cyclopentyl-hexanoic acid The title compound was obtained as a white foam after hydrogenolysis and preparative HPLC (280 mg, 89%). $^1$H-NMR; δ ((CD$_3$)$_2$SO, 60° C.), 7.77 (1H, d, J=8.3 Hz), 7.62 (2H, d, J=7.1 Hz), 7.53 (2H, d, J=8.2 Hz), 7.44 (2H, dd, J=7.1, 7.1 Hz), 7.32 (1H, d, J=7.2 Hz), 7.22 (7H, m,), 4.04 (1H, m), 3.45 (2H, m), 3.27 (2H, m), 2.93 (1H, ddd, J=4.6, 14.0 Hz), 2.66–2.47 (4H, m) and 1.10–1.00 (12H, m). $^{13}$C-NMR; δ ((CD$_3$)$_2$SO), 175.8, 173.7, 142.3, 141.0, 140.2, 138.4, 129.8, 128.8, 128.0, 127.4, 127.3, 126.7, 64.2, 54.8, 52.4, 48.1, 40.7, 37.2, 35.5, 31.8, 31.1, 29.3, 28.2, 25.7 and 25.3.

EXAMPLE 3

2S-Cyclopentyl-$N^1$-hydroxy-$N^4$-(1S-hydroxymethyl-2-phenyl-ethyl)-3R-isobutyl succinamide

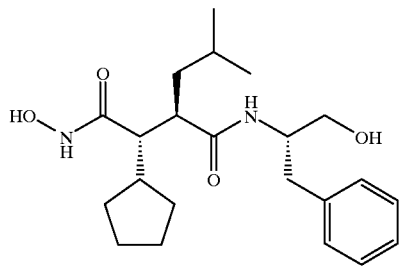

To a cooled solution of 2S-cyclopentyl-3R-(1S-hydroxymethyl-2-phenyl-ethylcarbamoyl)-5-methyl-hexanoic acid (Example 1) (399 mg, 1.06 mmol) in DMF (20 ml) was added HOBt (173 mg, 1.28 mmol) and EDC (245 mg, 1.28 mmol). The mixture was stirred at 0° C. for 15 minutes, then hydroxylamine hydrochloride (111 mg, 1.59 mmol) was added, followed by NMM (175 μl, 1.59 mmol) and the reaction mixture was allowed to warm to room temperature then stirred for 18 hours. The solvent was removed in vacuo and the residue was triturated between diethyl ether (12 ml) and water (4 ml). The resulting white precipitate was collected by filtration and dried under vacuum to give the title compound together with a minor impurity (total 119 mg) which were separable by preparative reverse phase HPLC. $^1$H-NMR; δ (CD$_3$OD), 7.16 (5H, m), 4.11 (1H, m), 3.46 (1H, dd, J=5.1, 10.7 Hz), 3.36 (1H, dd, J=7.0, 10.7 Hz), 2.91 (1H, dd, J=5.1, 14.4 Hz), 2.59 (1H, dd, J=9.7, 14.2 Hz), 2.47 (1H, m), 2.32 (1H, dd, J=5.9, 10.2 Hz), 1.57–0.89 (12H, br m), 0.77 (3H, d, J=6.4 Hz) and 0.73 (3H, d, J=6.5 Hz). $^{13}$C-NMR; δ (CD$_3$OD), 176.5, 175.7, 139.1, 129.1, 128.4, 126.4, 63.8, 53.1, 46.7, 41.1, 41.0, 38.2, 36.7, 30.9, 28.6, 28.1, 26.0, 25.3, 23.6 and 20.7.

The following compound was similarly prepared from 3R-(1S-Benzyl-2-hydroxy-ethylcarbamoyl)-6-biphenyl-4-yl-propyl-2S-cyclopentyl-hexanoic acid (Example 2):

EXAMPLE 4

$N^{1'}$-(1S-Benzyl-2-hydroxy-ethyl)-2R-(3-biphenyl-4-yl-propyl)-3S-cyclopentyl-$N^4$-hydroxy-succinamide

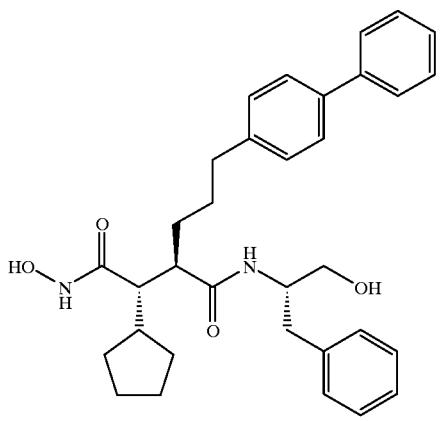

White solid. $^1$H-NMR; δ ((CD$_3$)$_2$SO, 60° C.), 7.61 (2H, m), 7.53 (2H, d, J=8.1 Hz), 7.43 (2H, dd, J=7.1, 7.1 Hz), 7.33 (1H, d, J=7.2 Hz), 7.21 (7H, m), 4.04 (1H, m), 3.46–2.91 (5H, m), 2.56–2.42 (4H, m) and 1.70–1.02 (12H, m). $^{13}$C-NMR; δ ((CD$_3$)$_2$SO), 175.8, 174.3, 142.4, 141.0, 140.3, 138.4, 129.8, 128.8, 128.1, 127.4, 127.3, 126.7, 64.2, 54.9, 52.4, 48.0, 40.7, 37.2, 35.5, 32.0, 31.1, 29.3, 28.3, 25.7 and 25.3.

What is claimed is:
1. A compound of general formula (I)

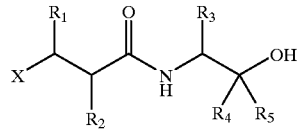

wherein:
X is a —CO$_2$H or —CONHOH group;
R$_1$ is a cycloalkyl, cycloalkenyl or non-aromatic heterocyclic ring containing up to 3 heteroatoms, any of which may be (i) substituted by one or more substituents selected from C$_1$–C$_6$ alkyl, C$_2$C$_6$ alkenyl, halo, cyano (—CN), —CO$_2$H, —CO$_2$R, —CONH$_2$, —CONHR, —CON(R)$_2$, —OH, —OR, oxo-, —SH, —SR, —NHCOR and —NHCO$_2$R wherein R is C$_1$–C$_6$ alkyl or benzyl and/or (ii) fused to a cycloalkyl or heterocyclic ring;
R$_2$ is a C$_1$–C$_{12}$ alkyl, C$_2$–C$_{12}$ alkenyl, C$_2$–C$_{12}$ alkenyl, phenyl(C$_1$–C$_6$ alkyl)-, heteroaryl(C$_1$–C$_6$ alkyl)-, cycloalkyl(C$_1$–C$_6$ alkyl)-, cycloalkenyl(C$_1$–C$_6$ alkyl)-, phenoxy(C$_1$–C$_6$ alkyl)-, heteroaryloxy(C$_1$–C$_6$ alkyl)-, phenyl(C$_1$–C$_6$ alkyl)O(C$_1$–C$_6$ alkyl)-, heteroaryl (C$_1$–C$_6$ alkyl)O(C$_1$–C$_6$ alkyl)-, phenyl(C$_1$–C$_6$ alkyl)S (C$_1$–C$_6$ alkyl)-, or heteroaryl(C$_1$–C$_6$ alkyl)S(C$_1$–C$_6$ alkyl)- group, any one of which may be optionally substituted by C$_1$–C$_6$ alkyl, C$_1$–C$_6$ alkoxy, halo, cyano (—CN), phenyl, substituted phenyl or heteroaryl.
R$_3$ is C$_1$–C$_6$ alkyl, benzyl, 2,- 3-, or 4-hydroxybenzyl, 2,- 3-, or 4-benzyloxybenzyl, 2,- 3-, or 4-C$_1$–C$_6$ alkoxybenzyl, or benzyloxy(C$_1$–C$_6$alkyl)-; or the characterizing group of a natural a amino acid, in which any functional group may be protected, any amino group may be acylated and any carboxyl group present may be amidated; or
a group —(Alk)$_n$R$_6$ where Alk is a (C$_1$–C$_6$)alkylene or (C$_2$–C$_6$)alkenylene group optionally interrupted by one or more —O—, or —S— atoms or —N(R$_7$)- groups, where R$_7$ is a hydrogen atom or a (C$_1$–C$_6$)alkyl group, n is 0 or 1, and R$_6$ is an optionally substituted cycloalkyl or cycloalkenyl group; or
a benzyl group subsituted in the phenyl ring by a group of formula —OCH$_2$COR$_8$ wherein R$_8$ is hydroxyl, amino, (C$_1$–C$_6$)alkoxy, phenyl(C$_1$–C$_6$)alkoxy, (C$_1$–C$_6$) alkylamino, di((C$_1$–C$_6$)alkyl)amino, phenyl(C$_1$–C$_6$) alkylamino, the residue of an amino acid or acid halide, ester or amide derivative thereof, said residue being linked via an amide bond, said amino acid being selected from glycine, α or β alanine, valine, leucine, isoleucine, phenylalanine, tyrosine, tryptophan, serine, threonine, cysteine, methionine, asparagine, glutamine, lysine, histidine, arginine, glutamic acid, and aspartic acid; or
a heterocyclic((C$_1$–C$_6$)alkyl group, either being unsubstituted or mono- or di-substituted in the heterocyclic ring with halo, nitro, carboxy, (C$_1$–C$_6$)alkoxy, cyano, (C$_1$–C$_6$)alkanoyl, trifluoromethyl (C$_1$–C$_6$)alkyl, hydroxy, formyl, amino, (C$_1$–C$_6$)alkylamino, di-(C$_1$–C$_6$)alkylamino, mercapto, (C$_1$–C$_6$)alkylthio, hydroxy(C$_1$–C$_6$)alkyl, mercapto(C$_1$–C$_6$)alkyl or (C$_1$–C$_6$)alkylphenylmethyl; or a group —CR$_a$R$_b$R$_c$ in which:
  each of R$_a$, R$_b$ and R$_c$ is independently hydrogen, (C$_1$–C$_6$)alkyl, (C$_2$C$_6$)alkenyl, (C$_2$–C$_6$)alkynyl, phenyl(C$_1$–C$_6$)alkyl, (C$_3$–C$_8$)cycloalkyl; or
  R$_c$ is hydrogen, (C$_1$–C$_6$)alkyl, (C$_2$–C$_6$)alkenyl, (C$_2$–C$_6$) alkynyl, phenyl(C$_1$–C$_6$)alkyl, or (C$_3$–C$_8$)cycloalkyl, and R$_a$ and R$_b$ together with the carbon atom to which they are attached form a 3 to 8 membered cycloalkyl or a 5- to 6-membered heterocyclic ring; or
  R$_a$, R$_b$ and R$_c$ together with the carbon atom to which they are attached form a tricyclic ring; or
  R$_a$ and R$_b$ are each independently (C$_1$–C$_6$)alkyl, (C$_2$–C$_6$)alkenyl, (C$_2$–C$_6$)alkynyl, phenyl (C$_1$–C$_6$) alkyl, or a group as defined for R$_c$ below other than hydrogen, or R$_a$ and R$_b$ together with the carbon atom to which they are attached form a cycloalkyl or heterocyclic ring, and R$_c$ is hydrogen, —OH, —SH, halogen, —CN, —CO$_2$H, (C$_1$–C$_4$)perfluoroalkyl, —CH$_2$OH, —CO$_2$(C$_1$–C$_6$)alkyl, —O(C$_1$–C$_6$)alkyl, —O(C$_2$–C$_6$)alkenyl, —S(C$_1$–C$_6$)alkyl, —SO (C$_1$–C$_6$)alkyl, —SO$_2$(C$_1$–C$_6$) alkyl, —S(C$_2$–C$_6$) alkenyl, —SO(C$_2$–C$_6$)alkenyl, —SO$_2$(C$_2$–C$_6$) alkenyl or a group —Q—W wherein Q represents a bond or —O—, —S—, —SO—or —SO$_2$— and W represents a phenyl, phenylalkyl, (C$_3$–C$_8$)cycloalkyl, (C$_3$–C$_8$)cycloalkylalkyl, (C$_4$–C$_8$)cycloalkenyl, (C$_4$–C$_8$)cycloalkenylalkyl, heteroaryl or heteroarylalkyl group, which group W may optionally be substituted by one or more substituents independently selected from, hydroxyl, halogen, —CN, —CO$_2$H, —CO$_2$(C$_1$–C$_6$)alkyl, —CONH$_2$, —CONH(C$_1$–C$_6$) alkyl, —CONH(C$_1$–C$_6$)alkyl)$_2$, —CHO, —CH$_2$OH, (C$_1$–C$_4$)perfluoroalkyl, —O(C$_1$–C$_6$)alkyl, —S(C$_1$–C$_6$)alkyl, —SO(C$_1$–C$_6$)alkyl, —SO$_2$ (C$_1$–C$_6$)alkyl, —NO$_2$, —NH$_2$, —NH(C$_1$–C$_6$)alkyl, —N((C$_1$–C$_6$)alkyl)$_2$, —NHCO(C$_1$–C$_6$)alkyl, (C$_1$–C$_6$)alkyl, (C$_2$–C$_6$)alkenyl, (C$_2$–C$_6$)alkynyl, (C$_3$–C$_8$)cycloalkyl, (C$_4$–C$_8$)cycloalkenyl, phenyl or benzyl;
R$_4$ is hydrogen or a C$_1$–C$_6$ alkyl group, phenyl (C$_1$–C$_6$ alkyl) or heterocyclyl (C$_1$–C$_6$ alkyl);
R$_5$ is hydrogen or a C$_1$–C$_6$ alkyl group;
or, when R$_5$ is hydrogen, R$_3$ and R$_4$ taken together with the carbon atoms to which they are attached form a 2-hydroxycyclohexyl or C$_6$ sugar (hexose) ring;
or R$_4$ and R$_5$ taken together with the carbon atom to which they are attached form a 5 or 6-members carbocyclic or heterocyclic ring;
or a pharmaceutically acceptable salt, hydrate or solvate thereof.

2. A compound as claimed in claim 1 wherein the stereochemistry is as follows:
C atom carrying the R$_1$ and X groups —S,
C atom carrying the R$_2$ group —R,
C atom carrying the R$_3$ group —S.

3. A compound as claimed in claim 1 wherein X is a group —CONHOH.

4. A compound as claimed in claim 1 wherein R$_1$ is cyclohexyl, 4-methylcyclohexyl, cyclooctyl, cycloheptyl, cyclobutyl, cyclopropyl, tetrahydropyranyl, tetrahydrothien-3-yl, 1,1-dioxo-tetrahydrothien-3-yl, N-acetyl-piperidin-4-yl, N-methylpiperidin-4-yl or morpholin-4-yl.

5. A compound as claimed in claim 1 wherein R$_1$ is cyclopentyl.

6. A compound as claimed in claim 1 wherein R$_2$ is n-pentyl, n-hexyl, n-heptyl, n-nonyl, n-decyl, phenylpropyl, 4-chlorophenylpropyl, 4-methylphenylpropyl, or 4-methoxyphenylpropyl.

7. A compound as claimed in claim 1 wherein R$_2$ is iso-butyl, n-octyl, benzyloxypropyl, phenoxybutyl or 4-phenyl-phenylpropyl.

8. A compound as claimed in claim 1 wherein R$_3$ is iso-butyl, 1-benzylthio-1-methylethyl, or 1-methylthio-1-methylethyl.

9. A compound as claimed in claim 1 wherein R$_3$ is t-butyl or 1-mercapto-1-methylethyl.

10. A compound as claimed in claim 1 wherein R$_4$ is hydrogen, methyl, ethyl, benzyl or pyridylmethyl.

11. A compound as claimed in claim 1 wherein R$_5$ is hydrogen or methyl.

12. A compound as claimed in claim 1 wherein R$_4$ and R$_5$ are both hydrogen.

13. A compound as claimed in claim 1 wherein R$_4$ and R$_5$ taken together with the carbon atom to which they are attached form a cyclopentyl, cyclohexyl or morpholino ring.

14. A compound as claimed in claim 1 wherein R$_5$ is hydrogen, and R$_3$ and R$_4$ taken together with the carbon atoms to which they are attached may form a 2-hydroxycyclohexyl or a glucose ring.

15. A compound as claimed in claim 1 or claim 2 wherein
R$_1$ is cyclopentyl, cyclohexyl or cyclopropyl;
R$_2$ is iso-butyl, n-octyl, n-nonyl, benzyloxypropyl, phenoxybutyl or 4-phenyl-phenylpropyl;
R$_3$ is t-butyl, 1-mercapto-1-methylethyl or the characterizing group of a natural α amino acid; and
R$_4$ and R$_5$ are both hydrogen or a pharmaceutically acceptable salt, hydrate or solvate thereof.

16. A compound selected from the group consisting of:
2S-Cyclopentyl-3R-(1S-hydroxymethyl-2-phenyl-ethylcarbamoyl)-5-methyl-hexanoic acid,
3R-(1S-Benzyl-2-hydroxy-ethylcarbamoyl)-6-biphenyl4-yl-propyl-2S-cyclopentyl-hexanoic acid,
2S-Cyclopentyl-N$^1$-hydroxy-N$^4$-(1S-hydroxymethyl-2-phenyl-ethyl)-3R-isobutyl succinamide,
N$^1$-(1S-Benzyl-2-hydroxy-ethyl)-2R-(3-biphenyl-4-yl-propyl)-3S-cyclopentyl-N$^4$-hydroxy-succinamide,
and pharmaceutically acceptable salts, hydrates and solvates thereof.

17. A compound selected from the group consisting of:
2S-Cyclopentyl-N$^1$-hydroxy-N$^4$-(1S-hydroxymethyl-2,2-dimethylpropyl)-3R-octyl-succinamide,
3R-(3-Biphenyl4-yl-propyl)2S-cyclopentyl-N$^1$-hydroxy-N$^4$-(1S-hydroxymethyl-2,2-dimethylpropyl)-succinamide,
2S-Cyclopentyl-N$^1$-hydroxy-N$^4$-[2-hydroxy-1S-imidazol-4-ylmethyl)-ethyl]-3R-isobutyl succinamide,
3R-(3-Biphenyl-4-yl-propyl)-2S-cyclopentyl-N$^1$-hydroxy-N$^4$-(2-hydroxy-1S-imidazol-4-ylmethyl)-ethyl]-3R-isobutyl succinamide,
2S-Cyclopentyl-N$^1$-hydroxy-N$^4$-[2-hydroxy-1S-(4-hydroxybenzyl)-ethyl]-3R-isobutyl-succinamide,
N$^4$-(1S-Benzyl-2-hydroxy-ethyl)-N$^1$-hydroxy-3R-isobutyl-2S-(tetrahydrothiophen-2-yl)-succinamide,
N$^4$-(1S-Benzyl-2R-hydroxy-butyl)-3R-(3-Biphenyl-4-yl-propyl)-2S-cyclopentyl-N$^1$-hydroxy-succinamide,
N$^4$-(1S-Benzyl-2S-hydroxy-butyl)-3R-(3-Biphenyl-4-yl-propyl)-2S-cyclopentyl-N$^1$-hydroxy-succinamide,
3R-(3-Biphenyl-4-yl-propyl)-2S-cyclopentyl-N$^1$-hydroxy-N$^4$-(1S-hydroxymethyl-3-methylbutyl)-succinamide,
6-Biphenyl-4-yl-2S-cyclopentyl-3R-(2S-hydroxymethyl)-pyrrolidine-1-carbonyl)-hexanoic acid hydroxyamide, 3R-(3-Biphenyl-4-yl-propyl)-N⁴-(1S-tert-butyl-2R-hydroxy-butyl)-2S-cyclopentyl-N¹-hydroxy-succinamide, 3R-(3-Biphenyl-4-yl-propyl)-N⁴-(1S-tert-butyl-2S-hydroxy-butyl)-2S-cyclopentyl-N¹-hydroxy-succinamide, and pharmaceutically acceptable salts, hydrates and solvates thereof.

18. A pharmaceutical composition comprising a compound as claimed in claim 1, together with a pharmaceutically acceptable carrier.

19. A composition as claimed in claim 19, adapted for oral administration.

* * * * *

UNITED STATES PATENT AND TRADEMARK OFFICE
CERTIFICATE OF CORRECTION

PATENT NO.    : 6,310,084 B1
DATED         : October 30, 2001
INVENTOR(S)   : Raymond Paul Beckett et al.

It is certified that error appears in the above-identified patent and that said Letters Patent is hereby corrected as shown below:

Column 24,
Line 39, "a amino acid" has been replaced with -- α amino acid --

Column 26,
Line 35, "bipheny14" has been replaced with -- biphenyl-4 --
Line 46, "Biphenyl4-yl-propyl)2S" has been replaced with
-- Biphenyl-4-yl-propyl)-2S --

Column 28,
Line 4, "claim 19" has been replaced with -- claim 18 --

Signed and Sealed this

Eighteenth Day of June, 2002

Attest:

JAMES E. ROGAN
Attesting Officer    Director of the United States Patent and Trademark Office